(12) United States Patent
Shao et al.

(10) Patent No.: US 10,639,303 B2
(45) Date of Patent: *May 5, 2020

(54) ALKALOIDS AND THEIR PREPARATION AND APPLICATION AS ANTI-HSV-1 AGENTS

(71) Applicant: OCEAN UNIVERSITY OF CHINA, Qingdao (CN)

(72) Inventors: Changlun Shao, Qingdao (CN); Changyun Wang, Qingdao (CN); Xiaofeng Mu, Qingdao (CN); Rufang Xu, Qingdao (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/722,034

(22) Filed: Oct. 2, 2017

(65) Prior Publication Data

US 2018/0028523 A1 Feb. 1, 2018

Related U.S. Application Data

(63) Continuation-in-part of application No. PCT/CN2016/077649, filed on Mar. 29, 2016.

(30) Foreign Application Priority Data

Sep. 6, 2015 (CN) .......................... 2015 1 0561145

(51) Int. Cl.
| | | |
|---|---|---|
| A61K 31/4704 | (2006.01) | |
| C07D 215/22 | (2006.01) | |
| C07D 405/06 | (2006.01) | |
| C12P 17/12 | (2006.01) | |
| C12P 17/16 | (2006.01) | |
| A61K 31/341 | (2006.01) | |
| C12R 1/645 | (2006.01) | |

(52) U.S. Cl.
CPC ........ A61K 31/4704 (2013.01); A61K 31/341 (2013.01); C07D 215/22 (2013.01); C07D 405/06 (2013.01); C12P 17/12 (2013.01); C12P 17/16 (2013.01); C12N 2710/16063 (2013.01); C12R 1/645 (2013.01)

(58) Field of Classification Search
CPC .. C07D 215/22; C07D 405/06; A61K 31/341; A61K 31/4704; C12P 17/12; C12P 17/16; C12R 1/645; C12N 2710/16063
See application file for complete search history.

(56) References Cited

U.S. PATENT DOCUMENTS

2003/0104082 A1* 6/2003 Squires ................. A61K 9/145
424/737

FOREIGN PATENT DOCUMENTS

| CN | 103554090 A | | 2/2014 | |
|---|---|---|---|---|
| CN | 103554090 B | * | 3/2017 | ............ A01N 43/42 |
| EP | WO2009060015 A | | 5/2009 | |
| JP | WO2006059400 A | | 6/2006 | |
| WO | wo 92/04327 | | 3/1992 | |

OTHER PUBLICATIONS

Of Ren et al, Virol Sin. Apr. 2010;25(2):107-14 Epub Apr. 9, 2010 (Year: 2010).*
Ozcelik et al, Pharmaceutical Biology, 2011; 49(4): 396-402 (Year: 2011).*
Scott Neff, et al, Aflaquinolones A-G: Secondary Metabolites from Marine and Fungicolous Isolates of *Aspergillus* Spp., J. Nat Prod. 2012, Mar. 23; 75(3): 466-472.

* cited by examiner

*Primary Examiner* — Jean P Cornet

(57) ABSTRACT

The present invention provides alkaloids with formula I, II, III, IV, or V and their pharmaceutically acceptable salts, their preparation and their uses as antivirus drugs, for example, for treatment of HSV-1 infection. The alkaloids with formula I were isolated from the fermentation of marine fungus *Scopulariopsis* sp. (TA01-33) by means of column chromatography, such as positive phase silica gel column chromatography, etc. Alkaloids with formula II, III, IV and V were semisynthesized from compounds with formula I.

1 Claim, No Drawings

ALKALOIDS AND THEIR PREPARATION AND APPLICATION AS ANTI-HSV-1 AGENTS

CROSS-REFERENCE TO RELATED APPLICATIONS

This is a continuation-in-part application of the International Patent Application No. PCT/CN/2016/077649, filed Mar. 29, 2016, which claims priority to Chinese Patent Application No. 201510561145.3, filed Sep. 6, 2015, both of which are incorporated herein by reference in their entirety.

FIELD OF INVENTION

The present invention relates to the field of anti-viral agents. In one embodiment, provided herein are alkaloids, their combinations, their methods of preparation and their uses as drugs, for example, for treatment of disease caused by HSV-1 virus.

BACKGROUND OF THE INVENTION

Herpes Simplex Virus 1 (HSV-1) is an enveloped DNA virus, with high incidence, long latency, perineural, and incubating in peripheral nervous system. Young children, organ transplant recipients or people with diminished immunity are susceptible to infection of HSV-1 virus. Once infected, HSV-1 virus can cause serious encephalitis, keratitis and even death. Nucleoside antiviral medications, such as acyclovir, famciclovir, and valacyclovir, are the most effective medications available for people infected with HSV. These medications can help to reduce the severity and frequency of symptoms, but cannot cure the infection. In view of the increasing cases of drug-resistant pathogens, it is imperative to develop new and effective antiviral drugs. Marine microorganisms are widely recognized as prolific sources of biologically active and structurally unique natural products because of their unique living condition such as high salinity, high pressure, low temperature, oxygen deficiency and darkness. However, there are few reports of marine-derived antiviral entity (Newman, D. J.; Cragg, G. M. *J. Nat. Prod.* (2012) 75:311-335; Blunt, J. W.; Copp, B. R.; Keyzers, R. A.; Munro, M. H. G.; Prinsep, M. R. *Nat. Prod. Rep.* (2014) 31:160-258, and previous annual reports). Thus, there is a need of developing new and effective antiviral drugs.

SUMMARY OF THE INVENTION

In one embodiment, provided herein are novel alkaloids or pharmaceutical compositions thereof with antiviral activity, for example, anti-HSV-1 activity which can be used as antiviral agents in treatment to disease caused by HSV-1. In one aspect, provided herein are compounds having Formula I, II, III, IV, or V as shown below:

Formula I

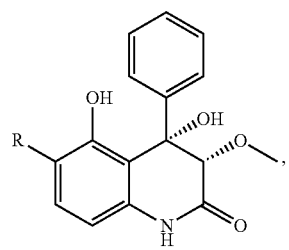

wherein R is

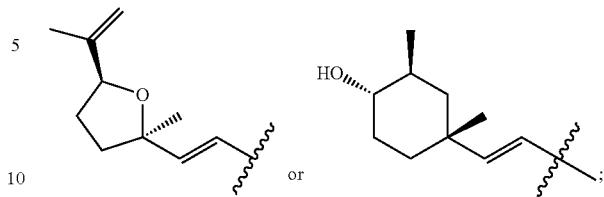

Formula II wherein R is

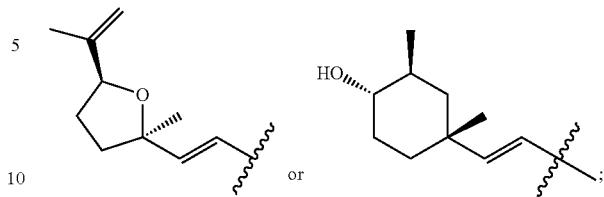

X is OH or $C_{1-4}$ alkoxy, Y is OH or $C_{1-4}$ alkoxy, Z is OH or $C_{1-4}$ alkoxy, W is OH or $C_{1-4}$ alkoxy;

Formula III

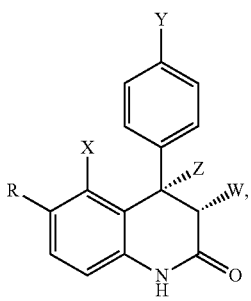

wherein R is

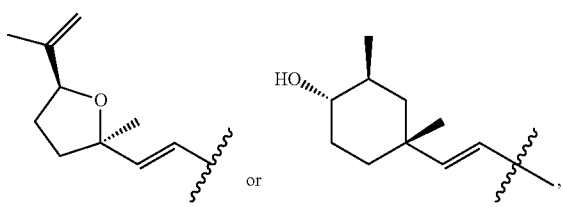 [SMILES: */C=C/[C@@]1(C)CC[C@@H](C(=C)C)O1 ; */C=C/[C@]1(C)CC[C@H](O)[C@@H](C)C1]

X is OH or $C_{1-4}$ acyloxy, Y is OH or $C_{1-4}$ acyloxy, Z is OH or $C_{1-4}$ acyloxy, W is OH or $C_{1-4}$ acyloxy;

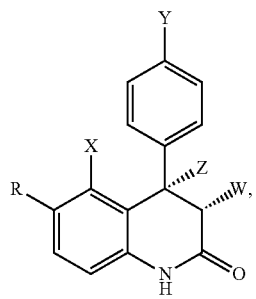

Formula IV wherein R is

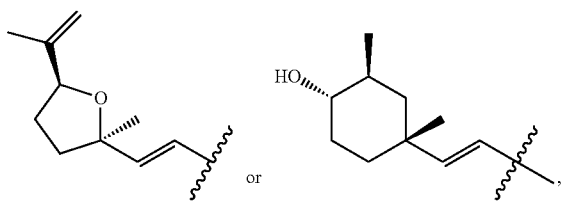 [SMILES: */C=C/[C@@]1(C)CC[C@@H](C(=C)C)O1 ; */C=C/[C@]1(C)CC[C@H](O)[C@@H](C)C1]

X is OH, $C_{1-4}$ alkoxy or $C_{1-4}$ acyloxy, Y is halogen (such as Cl, Br, F) or OH, Z is OH, $OCH_3$, $C_{1-4}$ alkoxy or $C_{1-4}$ acyloxy, W is OH, $C_{1-4}$ alkoxy or $C_{1-4}$ acyloxy;

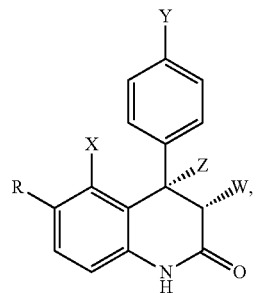

Formula V wherein R is

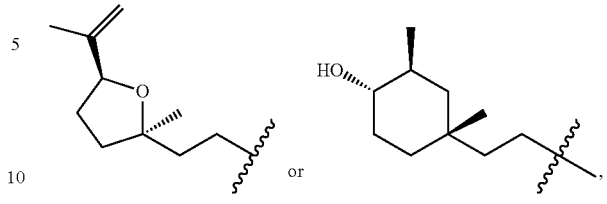

X is OH, $C_{1-4}$ alkoxy or $C_{1-4}$ acyloxy, Y is H, OH, halogen (such as Cl, Br, F), $C_{1-4}$ alkoxy or $C_{1-4}$ acyloxy, Z is OH, $OCH_3$, $C_{1-4}$ alkoxy or $C_{1-4}$ acyloxy, W is OH, $C_{1-4}$ alkoxy or $C_{1-4}$ acyloxy.

Novel alkaloids provided herein include, but are not limited to, stereoisomers, geometric isomers, tautomers or the combination of their mixtures. The chiral carbon at certain position of the molecule can be formed by semisynthesis with racemic mixture, enantiomer or diastereoisomer. Compounds provided herein can be separated by means of conventional methods, such as chromatography, chemical resolution and fractionated crystallization.

In one embodiment, the present invention provides a method of treating an infection of Herpes Simplex Virus 1 (HSV-1), comprising administering to a subject in need thereof an effective amount of a compound, or pharmaceutically acceptable salts thereof, having a structure of wherein R is a monoterpenoid side chain or oxy-derivatives; X or Z or W is hydroxyl, or is a hydroxyl derivative or hydroxyl derivatives; and Y is H, halogen or is hydroxyl derivative The present invention also provides a method of treating an infection of Herpes Simplex Virus 1 (HSV-1), comprising administering to a subject in need thereof an effective amount of a compound, or pharmaceutically acceptable salts thereof, having a structure of Formula I, II, III, IV, or V as disclosed herein.

In another embodiment, there is provided a method of inhibiting activities of herpes simplex virus 1 (HSV-1), comprising the step of contacting a cell with a compound, or pharmaceutically acceptable salts thereof, having a structure of

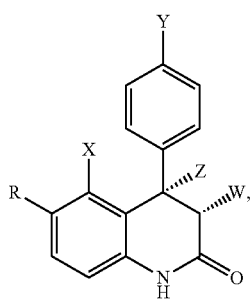

wherein R is a monoterpenoid side chain or oxy-derivatives; X or Z or W is hydroxyl, or is a hydroxyl derivative or hydroxyl derivatives; and Y is H, halogen or is hydroxyl derivative.

In another embodiment, there is provided a method of inhibiting activities of herpes simplex virus 1 (HSV-1), comprising the step of contacting a cell with a compound, or pharmaceutically acceptable salts thereof, having a structure of Formula I, II, III, IV, or V as disclosed herein.

DETAILED DESCRIPTION OF THE INVENTION

The term "pharmaceutically acceptable salt" refers to organic or inorganic salts of a compound disclosed herein. Pharmaceutically acceptable salts are well known in the art. For example, details of pharmaceutically acceptable salts were described in "Salt selection for basic drugs", Int. J. Pharm. (1986), 33, 201-217, which is incorporated herein by reference.

The alkaloids with formula I provided herein are natural products, which were isolated from marine fungus *Scopulariopsis* sp. (TA01-33) derived from coral *Carijoa* sp. The fungus *Scopulariopsis* sp. (TA01-33) was first cultured in basal liquid medium (including glucoside 0.1%-5.0%, yeast extract 0.01%-1%, peptone 0.01%-1%, agar 0.1%-3.0%, sodium chloride 3%-5%) under 0-30° C. for 3-15 days to obtain single strain. Then the single strain was cultured in fermentation medium (including glucoside 0.1%-5.0%, yeast extract 0.01%-1%, peptone 0.01%-1%, agar 0.1%-3.0%, sodium chloride 3%-5%) under 0-30° C. for 6-30 days. Fungal mycelia were extracted three times with ethyl acetate. The organic extracts were combined and concentrated under vacuum to obtain a dry extract. The extract was subjected to silica gel column chromatography (200-300 mesh, mobile phase: ethyl acetate-petroleum (5%-95%)), Sephadex LH-20 chromatography (mobile phase: petroleum-dichloromethane-methanol (v:v:v=2:1:1)) and high performance liquid chromatography (HPLC) (ODS C18 column, Kromasil 250×10 mm, 7 μm, 1-5 mL/min) to obtain compounds with formula I. Compounds with formula II, III, IV, V were semisynthesized from compounds with formula I.

The fungal strain (TA01-33) was isolated from a piece of fresh tissue from the inner part of the gorgonian *Carijoa* sp., collected from the Weizhou coral reef in the South China Sea in April 2010. The strain was identified as *Scopulariopsis* sp. according to morphologic traits and molecular identification. The strain was deposited at Microbial Preservation Management Committee, General Microbiology Centre in China, The Chinese Academy of Sciences Institute of Microbiology, No. 1 Beichen West Road, Chaoyang district, Beijing (date: Dec. 17, 2012; Strain Number: CGMCC6959).

In one embodiment, there is provided a method of treating an infection of Herpes Simplex Virus 1 (HSV-1), comprising administering to a subject in need thereof an effective amount of a compound, or pharmaceutically acceptable salts thereof, having a structure of

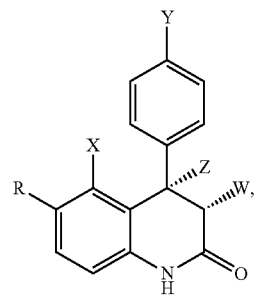

wherein R is a monoterpenoid side chain or oxy-derivatives; X or Z or W is hydroxyl, or is a hydroxyl derivative or hydroxyl derivatives; and Y is H, halogen or is hydroxyl derivative.

In one embodiment, the above compound has a structure of the following formula I, Formula I

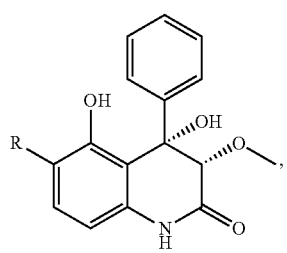

wherein R is

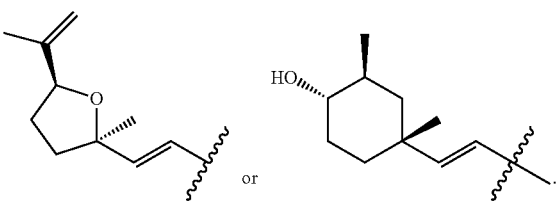 [SMILES: */C=C/[C@@]1(C)CC[C@@H](C(=C)C)O1 ; */C=C/[C@]1(C)CC[C@H](O)[C@@H](C)C1]

In one embodiment, the above compound has a structure of the following formula II, Formula II

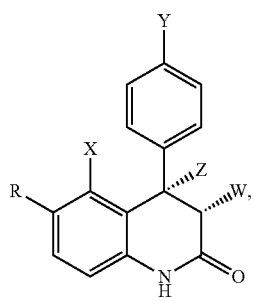

wherein R is

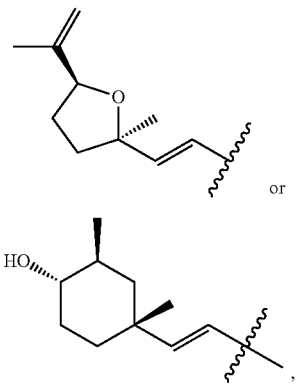

or

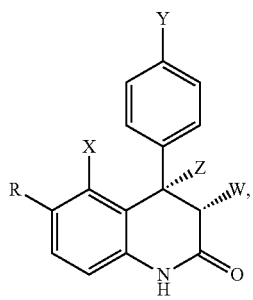

and each of X, Y, Z, or W is OH or C$_{1-4}$ alkoxy.

In one embodiment, the above compound has a structure of the following formula III, Formula III

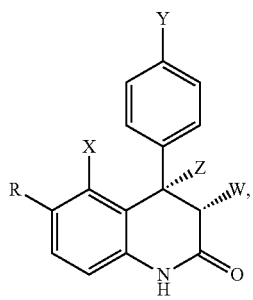

wherein R is

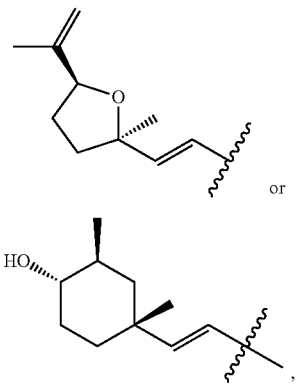

or

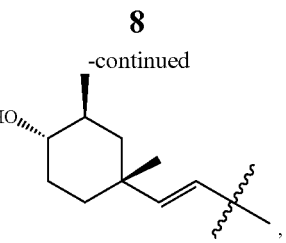

, and each of X, Y, Z, or W is OH or C$_{1-4}$ acyloxy.

In one embodiment, the above compound has a structure of the following formula IV, Formula IV

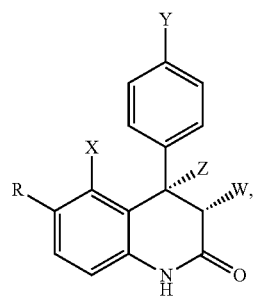

wherein R is

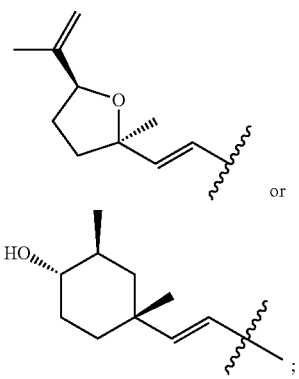

or

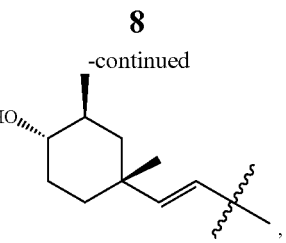

;

X is OH, C$_{1-4}$ alkoxy, or C$_{1-4}$ acyloxy; Y is halogen (such as Cl, Br, F) or OH; Z is OH, OCH$_3$, C$_{1-4}$ alkoxy, or C$_{1-4}$ acyloxy; and W is OH, C$_{1-4}$ alkoxy, or C$_{1-4}$ acyloxy.

In one embodiment, the above compound has a structure of the following formula V, Formula V

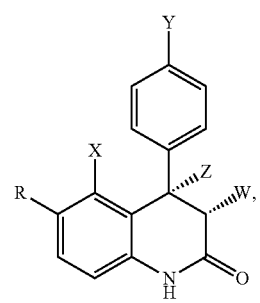

wherein R is

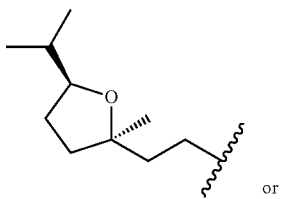 or

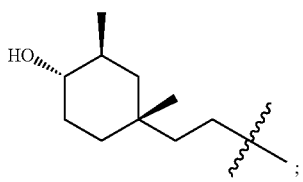 ;

X is OH, $C_{1-4}$ alkoxy, or $C_{1-4}$ acyloxy; Y is H, OH, halogen (such as Cl, Br, F), $C_{1-4}$ alkoxy, or $C_{1-4}$ acyloxy; Z is OH, $C_{1-4}$ alkoxy or C1-4 acyloxy; W is OH, C1-4 alkoxy, or $C_{1-4}$ acyloxy.

In another embodiment, there is provided a method of inhibiting activities of herpes simplex virus 1 (HSV-1), comprising the step of contacting a cell with a compound, or pharmaceutically acceptable salts thereof, having a structure of

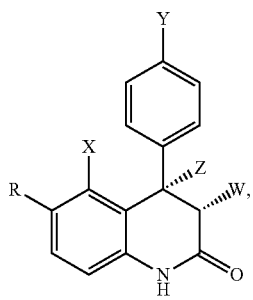

wherein R is a monoterpenoid side chain or oxy-derivatives; X or Z or W is hydroxyl, or is a hydroxyl derivative or hydroxyl derivatives; and Y is H, halogen or is hydroxyl derivative.

In one embodiment, the above compound has a structure of the following formula I, Formula I

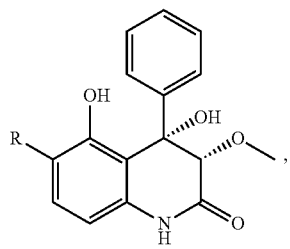

wherein R is

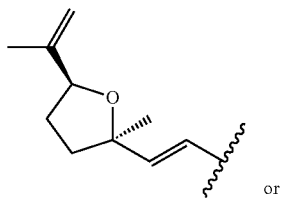 or

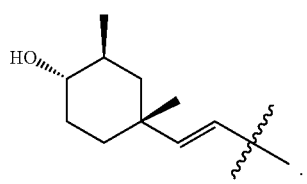 .

In one embodiment, the above compound has a structure of the following formula II, Formula II

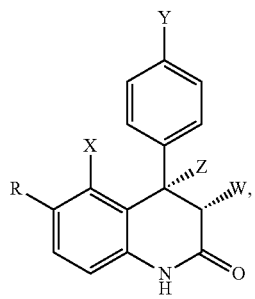

wherein R is

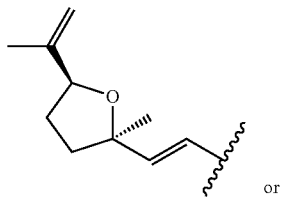 or

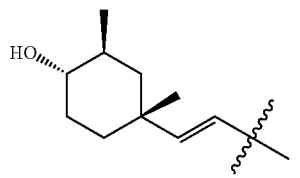 , and each of X, Y, Z, or W is OH or $C_{1-4}$ alkoxy.

In one embodiment, the above compound has a structure of the following formula III, Formula III

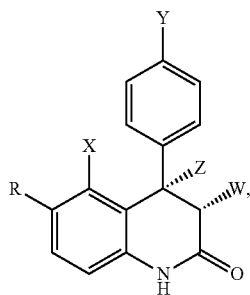

wherein R is

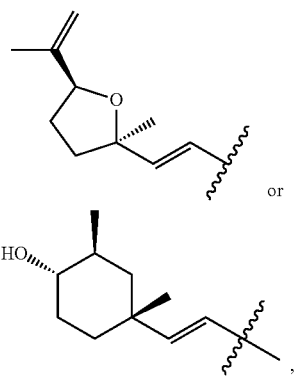

and each of X, Y, Z, or W is OH or $C_{1-4}$ acyloxy.

In one embodiment, the above compound has a structure of the following formula IV, Formula IV

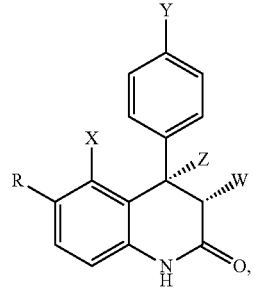

wherein R is

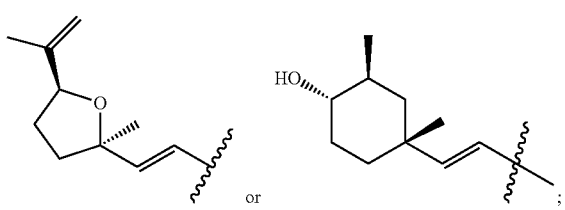 [SMILES: */C=C/[C@@]1(C)CC[C@@H](C(=C)C)O1 ; */C=C/[C@]1(C)CC[C@H](O)[C@@H](C)C1]

X is OH, C1-4 alkoxy, or C1-4 acyloxy; Y is halogen (such as Cl, Br, F) or OH; Z is OH, OCH$_3$, C1-4 alkoxy, or C1-4 acyloxy; and W is OH, $C_{1-4}$ alkoxy, or $C_{1-4}$ acyloxy.

In one embodiment, the above compound has a structure of the following formula V, Formula V

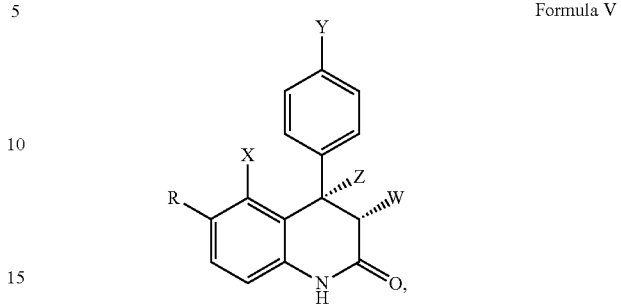

wherein R is

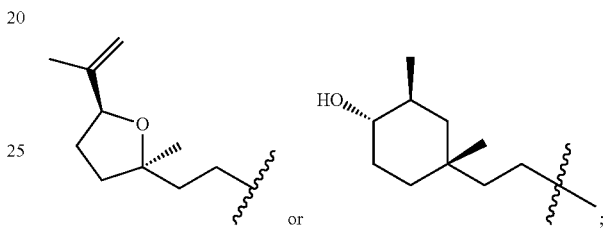

X is OH, C1-4 alkoxy, or C1-4 acyloxy; Y is H, OH, halogen (such as Cl, Br, F), C1-4 alkoxy, or C1-4 acyloxy; Z is OH, C1-4 alkoxy or C1-4 acyloxy; W is OH, $C_{1-4}$ alkoxy, or $C_{1-4}$ acyloxy.

The present invention also provides the compounds disclosed herein and methods for preparing the same, comprising one or more of the following steps: causing marine fungus Scopulariopsis sp. (TA01-33) to undergo fermentation, then the fermentation extracts of marine fungus Scopulariopsis sp. (TA01-33) are concentrated and subjected to means of chromatography, such as silica gel chromatography, Sephadex LH-20 chromatography, and then generating alkaloids with the formula I through HPLC. In one embodiment, compounds with formula I are dissolved in aprotic solvent, such as DMF, acetone, DCM and the like, and halogenated alkane or acyl chloride is added under the catalysis of K$_2$CO$_3$, thereby obtaining halogenated, alkoxy substituted or acyloxy substituted alkaloids as disclosed herein. In another embodiment, compounds with formula I are dissolved in mercaptan, and BBr3 is added under low temperature, thereby obtaining demethylation derivatives of alkaloids as disclosed herein. In another embodiment, compounds with formula I are dissolved in MeOH, and Pd/C (10%) is added under H$_2$, thereby obtaining hydrogenated derivatives of alkaloids as disclosed herein.

The invention may be more completely understood in consideration of the following detailed description of various embodiments of the disclosure in connection with the accompanying drawings.

EXAMPLES

The following example illustrates the invention further. Accordingly, it is to be understood that the embodiments of the present disclosure are not to be limited to the following described exemplary embodiments, but is to be controlled by the limitations set forth in the claims and any equivalents thereof.

Example 1

The alkaloids with formula I provided herein are natural products, which were isolated from marine fungus *Scopulariopsis* sp. (TA01-33) derived from coral *Carijoa* sp. The fungus *Scopulariopsis* sp. (TA01-33) was first cultured in basal liquid medium (including glucoside 1.0%, yeast extract 0.2%, peptone 0.2%, agar 1.0%, sodium chloride 3%) under 30° C. for 5 days to obtain single strain. Then the single strain was cultured in fermentation medium (including glucoside 1.0%, yeast extract 0.2%, peptone 0.2%, agar 1.0%, sodium chloride 3%) under 28° C. for 60 days. The fungal mycelia were concentrated and extracted five times with equal volume of ethyl acetate. The organic extracts were combined and concentrated under vacuum to obtain a dry extract. The extract was subjected to silica gel column chromatography (200-300 mesh, mobile phase: ethyl acetate-petroleum (v:v=40%:60%), Sephadex LH-20 chromatography (mobile phase: petroleum/dichloromethane/methanol (v:v:v=2:1:1)) and high performance liquid chromatography (HPLC) (ODS C18 column, Kromasil 250×10 mm, 7 μm, mobile phase: 70% or 80% (v %) methanol-water, 2 mL/min) to obtain compounds with formula I.

The compounds were characterized by the following spectroscopic data:

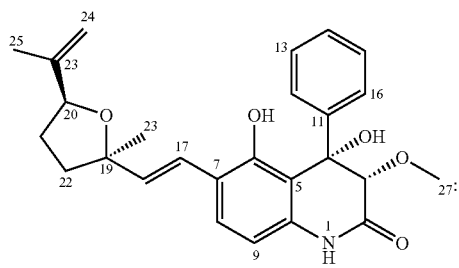 [SMILES: C=C(C)[C@@H]1CC[C@](C)(/C=C/c2ccc3c(c2O)[C@@](O)(c2ccccc2)[C@H](OC)C(=O)N3)O1]

colorless crystal, $[\alpha]^{24}D=+133.5$ (c 0.017, MeOH); $^1$H NMR (acetone-d$_6$, 400 MHz, TMS) $\delta_H$ 3.67 (1H, s, H-3), 7.42 (1H, d, J=8.0 Hz, H-8), 6.57 (1H, d, J=8.0 Hz, H-9), 7.34 (5H, m, overlap, H-12,13,14,15,16), 6.87 (1H, d, J=16.4 Hz, H-17), 6.35 (1H, d, J=16.4 Hz, H-18), 4.42 (1H, t, J=7.2 Hz, H-20), 2.08 (1H, m, H-21a), 1.75 (1H, m, H-21b), 1.98 (1H, q, J=4.4 Hz, H-22a), 1.89 (1H, m, H-22b), 5.05 (1H, m, H-24a), 4.75 (1H, m, H-24b), 1.73 (3H, s, H-25), 1.35 (3H, s, H-26), 3.51 (3H, s, H-27); $^{13}$C NMR (acetone-d$_6$, 100 MHz, TMS) $\delta_C$ 166.3 (C-2), 85.6 (C-3), 79.9 (C-4), 112.0 (C-5), 156.9 (C-6), 121.5 (C-7), 127.9 (C-8), 107.7 (C-9), 137.1 (C-10), 140.1 (C-11), 129.5 (C-12,16), 127.4 (C-13,15), 129.7 (C-14), 121.6 (C-17), 135.9 (C-18), 83.6 (C-19), 82.7 (C-20), 31.8 (C-21), 39.3 (C-22), 147.2 (C-23), 110.2 (C-24), 18.6 (C-25), 27.3 (C-26), 58.9 (C-27); IR (KBr) $v_{max}$ 3288, 2970, 1721, 1689, 1618, 1379 and 1082 cm$^{-1}$; UV (MeOH) $\lambda_{max}$ (log ε): 211 (0.41), 233.6 (0.26), 280.9 (0.20), 287.4 (0.19), 322 (0.21) nm; EIMS m/z 435 [M]$^{·+}$; HREEIMS m/z 436.2114 [M+H]$^+$ (calcd for C$_{26}$H$_{29}$NO$_5$, 436.2118).

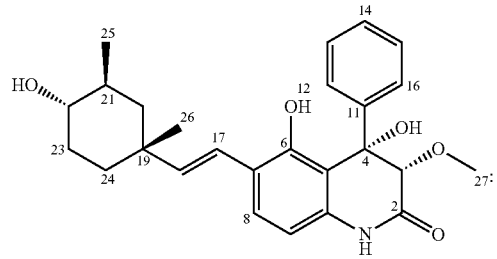 [SMILES: CO[C@@H]1C(=O)Nc2ccc(/C=C/[C@]3(C)CC[C@H](O)[C@@H](C)C3)c(O)c2[C@@]1(O)c1ccccc1]

colorless crystal; $[\alpha]^{24}_D=+133.5$ (c 0.017, MeOH); $^1$H NMR (acetone-d$_6$, 400 MHz, TMS) $\delta_H$ 3.66 (1H, d, J=1.2 Hz, H-3), 7.43 (1H, d, J=8.0 Hz, H-8), 6.57 (1H, d, J=8.0 Hz, H-9), 7.35 (5H, m, overlap, H-12,13,14,15,16), 6.63 (1H, d, J=16.4 Hz, H-17), 6.20 (1H, d, J=16.4 Hz, H-18), 1.07 (1H, t, J=12.8 Hz, H-20a), 1.74 (1H, m, H-20b), 1.54 (1H, m, H-21), 3.02 (1H, m, H-22), 1.71 (1H, m, H-23a), 1.49 (1H, m, H-23b), 1.78 (1H, m H-24a), 1.39 (1H, qd, J=13.6, 3.2 Hz, H-24b), 1.01 (3H, s, H-25), 0.96 (3H, d, J=6.8 Hz, H-26), 3.52 (3H, s, H-27); $^{13}$C NMR (acetone-d$_6$, 100 MHz, TMS) $\delta_C$ 166.3 (C-2), 85.7 (C-3), 80.0 (C-4), 112.1 (C-5), 155.9 (C-6), 122.3 (C-7), 127.4 (C-8), 107.7 (C-9), 136.8 (C-10), 140.2 (C-11), 129.5 (C-12,16), 127.4 (C-13,15), 129.6 (C-14), 122.5 (C-17), 137.5 (C-18), 37.7 (C-19), 46.9 (C-20), 36.9 (C-21), 76.7 (C-22), 33.0 (C-23), 37.7 (C-24), 31.8 (C-25), 19.3 (C-26), 58.9 (C-27); IR(KBr) $v_{max}$ 3366, 2926, 1687, 1600, 1421 and 1107 cm$^{-1}$; UV (MeOH) $\lambda_{max}$ (log ε): 204.8 (0.69), 211.2 (0.64), 252.8 (0.13), 281.6 (0.05) nm; EIMS m/z 437 [M]$^{·+}$; HREIMS m/z 437.2200 [M]$^{·+}$ (calcd for C$_{26}$H$_{31}$NO$_5$, 437.2197).

Example 2

The alkaloids with formula I provided herein are natural products, which were isolated from marine fungus *Scopulariopsis* sp. (TA01-33) derived from coarl *Carijoa* sp. The fungus *Scopulariopsis* sp. (TA01-33) was firstly cultured in basal liquid medium (including glucoside 0.1%-5.0%, yeast extract 0.01%-1%, peptone 0.01%-1%, agar 0.1%-3.0%, sodium chloride 3%-5%) under 0-30° C. for 3-15 days to obtain single strain. Then the single strain was cultured in fermentation medium (including glucoside 0.1%-5.0%, yeast extract 0.01%-1%, peptone 0.01%-1%, agar 0.1%-3.0%, sodium chloride 3%-5%) under 0~30° C. for 10-60 days. The fungal mycelia were extracted with 1-3 volume of ethyl acetate 2-5 times. The organic extracts were combined and concentrated under vacuum to obtain a dry extract. The extract was subjected to silica gel column chromatography (200-300 mesh, mobile phase: ethyl acetate-petroleum (5%-95%)), Sephadex LH-20 chromatography (mobile phase: petroleum-dichloromethane-methanol (v:v:v=2:1:1)) and high performance liquid chromatography (HPLC) (ODS C18 column, Kromasil 250×10 mm, 7 μm, 1-5 mL/min) to obtain compounds with colorless crystal form. The physical and chemical characteristics of the colorless crystal should be consistent with the compounds obtained in Example 1.

Culture conditions or column chromatography conditions not mentioned in Examples 1 and 2 are generally known in the art, and one of ordinary skill in the art would readily derive or adjust suitable conditions for the required culture or column chromatography.

Example 3

Compounds with formula I were obtained by methods provided in Example 1 and 2. Compounds with formula II, III, IV, V were semisynthesized by addition reaction, substitution reaction, and acylation reaction of compounds with formula I.

Compounds with Formula II

1) Compounds with formula I (0.1 mol) were dissolved in DMF, K₂CO₃ was added and CH₃I was added dropwise over a period of 10 min at room temperature. The reaction mixture was stirred at room temperature for 1-5 h, then quenched with water and extracted with ethyl acetate. The combined organic phases were concentrated in vacuo to give rough products. The products were then subjected to silica gel chromatography to give pure methylate product of compounds with formula I.

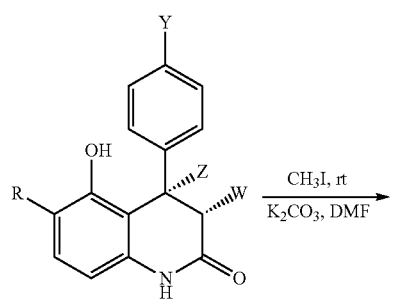

The compounds were characterized by the following spectroscopic data:

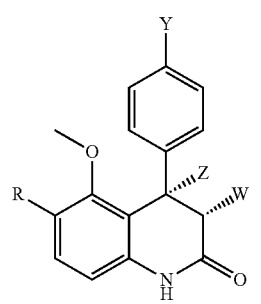

white powder, $[\alpha]^{24}_D$=+102.5 (c 0.017, MeOH); IR (KBr) $v_{max}$ 2970, 1730, 1689, 1618, 1400 and 1080 cm$^{-1}$; UV (MeOH) $\lambda_{max}$ (log ε): 211 (0.41), 233.6 (0.26), 280.9 (0.20), 285.4 (0.19), 325 (0.21) nm; EIMS m/z 464 [M]$^{•+}$.

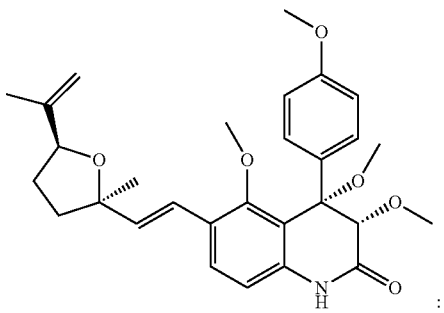 [SMILES: C=C(C)[C@@H]1CC[C@](C)(/C=C/c2ccc3c(c2OC)[C@@](OC)(c2ccc(OC)cc2)[C@H](OC)C(=O)N3)O1]

white powder, $[\alpha]^{24}_D$=+103.5 (c 0.017, MeOH); IR (KBr) $v_{max}$ 2970, 1721, 1690, 1618, 1375 and 1082 cm$^{-1}$; UV (MeOH) $\lambda_{max}$ (log ε): 211 (0.41), 233.6 (0.26), 280.9 (0.20), 287.4 (0.19), 320 (0.21) nm; EIMS m/z 494 [M]$^{•+}$.

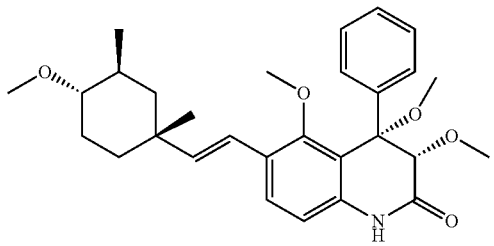

colorless crystal; $[\alpha]^{24}_D$=+123 (c 0.012, MeOH); IR(KBr) $v_{max}$ 2926, 1687, 1620, 1421 and 1102 cm$^{-1}$; UV (MeOH) $\lambda_{max}$ (log ε): 202.8 (0.69), 211.2 (0.64), 255.8 (0.13), 284.6 (0.05) nm; EIMS m/z 479 [M]$^{•+}$.

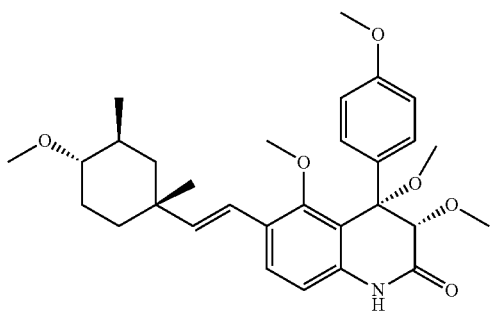

colorless crystal; $[\alpha]^{24}_D$=+104.5 (c 0.014, MeOH); IR(KBr) $v_{max}$ 2926, 1687, 1600, 1421 and 1107 cm$^{-1}$; UV (MeOH) $\lambda_{max}$ (log ε): 202.8 (0.69), 211.2 (0.64), 255.8 (0.13), 284.4 (0.05) nm; EIMS m/z 509 [M]$^{•+}$.

2) Compounds with formula I (0.1 mol) were dissolved in mercaptan, BBr3 was added and the reaction mixture was stirred at −70° C. overnight. The rough products were then subjected to silica gel chromatography to give pure demethylation product of compounds with formula I.

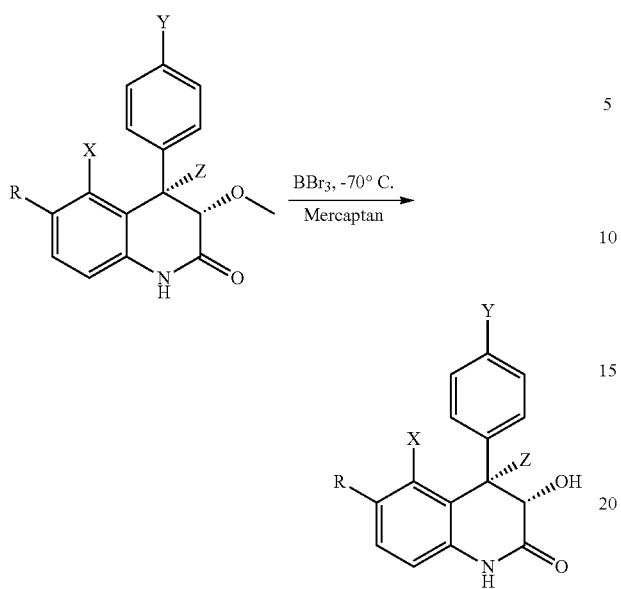

The compounds were characterized by the following spectroscopic data:

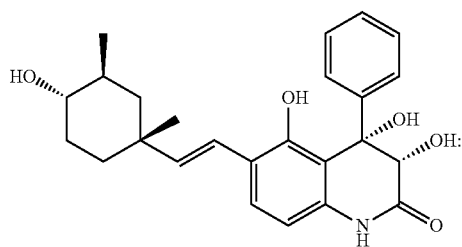

$[\alpha]^{24}_D$=+95 (c 0.014, MeOH); IR(KBr) $v_{max}$ 3350, 2900, 1630, 1450 and 1135 cm$^{-1}$; UV (MeOH) $\lambda_{max}$ (log ε): 200.8 (0.69), 215.2 (0.64), 250.5 (0.13), 282 (0.05) nm; EIMS m/z 422 [M]$^{·+}$.

$[\alpha]^{24}_D$=+130 (c 0.014, MeOH); IR(KBr) $v_{max}$ 3360, 2929, 1650, 1410 and 1105 cm$^{-1}$; UV (MeOH) $\lambda_{max}$ (log ε): 204.8 (0.69), 211.2 (0.64), 254 (0.13), 270 (0.05) nm; EIMS m/z 423 [M]$^{·+}$.

Compounds with Formula III

Compounds with formula I (0.1 mol) were dissolved in acetone, K$_2$CO$_3$ was added, and acetic anhydride was added at room temperature. The reaction mixture was stirred at room temperature for 1-5 h, then quenched with water and extracted with ethyl acetate. The combined organic phases were concentrated in vacuo to give rough products. The products were then subjected to silica gel chromatography to give pure acetylation product of compounds with formula I.

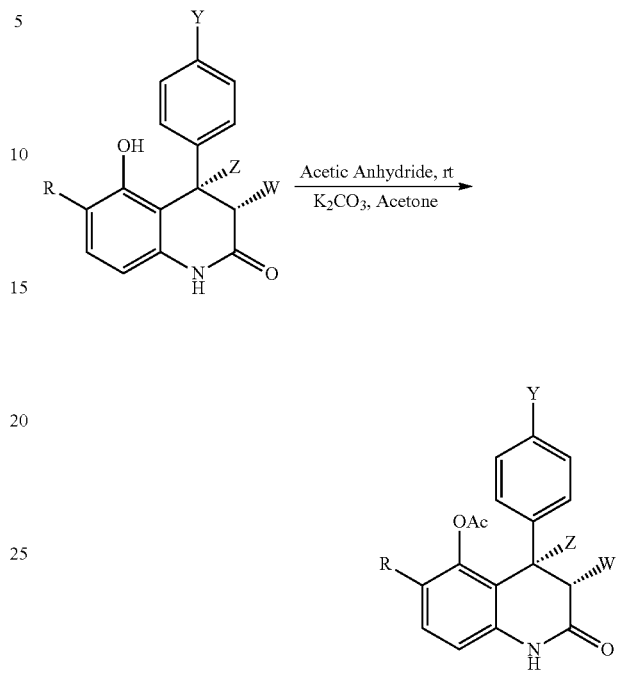

The compounds were characterized by the following spectroscopic data:

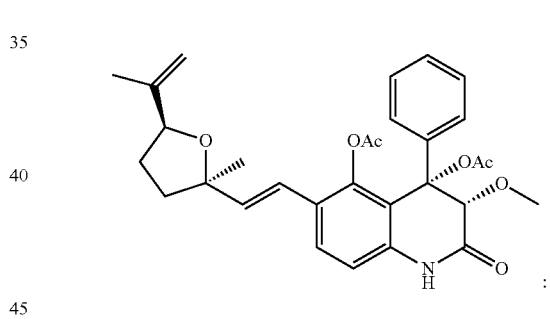

white powder; $[\alpha]^{24}_D$=+130.5 (c 0.022, MeOH); IR (KBr) $v_{max}$ 2970, 1720, 1618, 1379 and 1085 cm$^{-1}$; UV (MeOH) $\lambda_{max}$ (log ε): 211 (0.41), 233.6 (0.26), 280.9 (0.20), 285 (0.19), 325 (0.21) nm; EIMS m/z 520 [M]$^{·+}$.

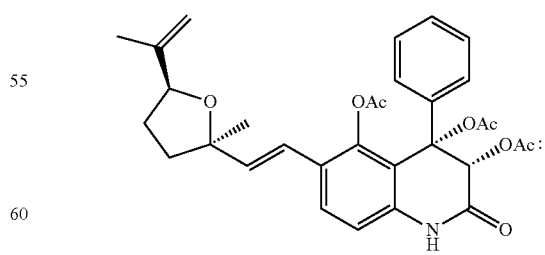

white powder; $[\alpha]^{24}_D$=+130 (c 0.015, MeOH); IR (KBr) $v_{max}$ 2970, 1721, 1618, 1380 and 1082 cm$^{-1}$; UV (MeOH) $\lambda_{max}$ (log ε): 211 (0.41), 234 (0.26), 282.4 (0.20), 285 (0.19), 325 (0.21) nm; EIMS m/z 606 [M]$^{·+}$.

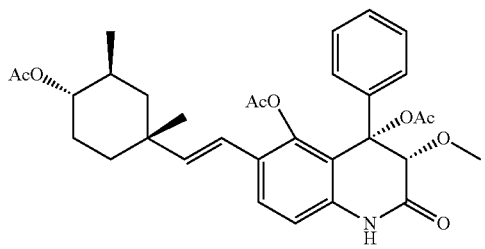

white powder; $[\alpha]^{24}_D$=+123.5 (c 0.014, MeOH); IR(KBr) $v_{max}$ 2926, 1675, 1600, 1420 and 1100 cm$^{-1}$; UV (MeOH) $\lambda_{max}$ (log ε): 202.8 (0.69), 211.2 (0.64), 255 (0.13), 281.6 (0.05) nm; EIMS m/z 564[M]$^{\cdot+}$.

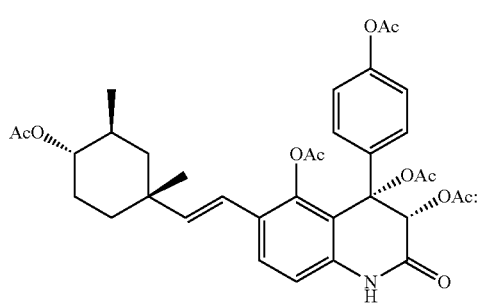

white powder; $[\alpha]^{24}_D$=+100.5 (c 0.016, MeOH); IR(KBr) $v_{max}$ 2926, 1687, 1620, 1421 and 1110 cm$^{-1}$; UV (MeOH) $\lambda_{max}$ (log ε): 204.8 (0.69), 215.2 (0.64), 252.8 (0.13), 285.6 (0.05) nm; EIMS m/z 650 [M]$^{\cdot+}$.

Compounds with Formula IV

1) Compounds with formula I, II or III (0.1 mol) were dissolved in DCM, and sulfonyl chloride (1N) was added in an ice bath. The reaction mixture was stirred in the ice bath for 3-5 h, then quenched with saturated ammonium chloride solution and extracted with ethyl acetate. The combined organic phases were concentrated in vacuo to give rough products. The products were then subjected to silica gel chromatography to give pure halogenate product of compounds with formula I.

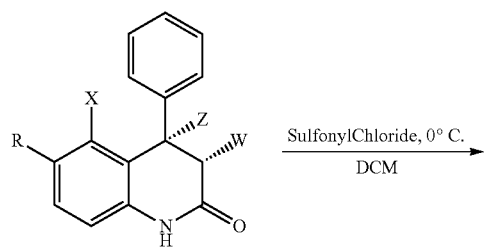

The compounds were characterized by the following spectroscopic data:

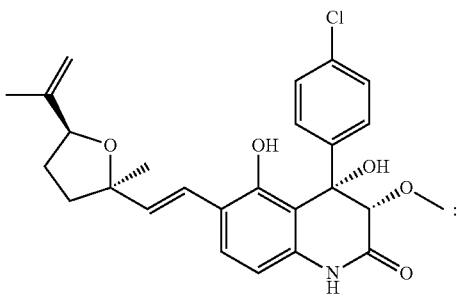

$[\alpha]^{24}_D$=+130 (c 0.014, MeOH); IR(KBr) $v_{max}$ 3360, 2929, 1650, 1410 and 1105 cm$^{-1}$; UV (MeOH) $\lambda_{max}$ (log ε): 204.8 (0.69), 211.2 (0.64), 254 (0.13), 270 (0.05) nm; EIMS m/z 471.6 [M]$^{\cdot+}$.

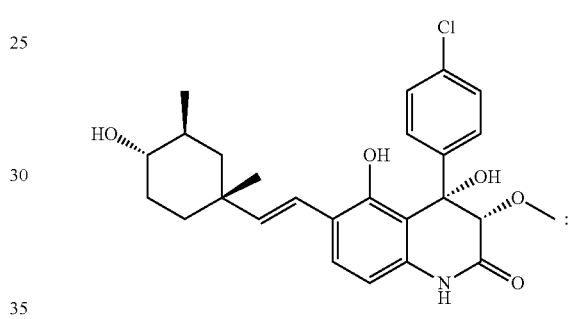

$[\alpha]^{24}_D$=+100.2 (c 0.020, MeOH); IR(KBr) $v_{max}$ 3330, 2900, 1620, 1415 and 1105 cm$^{-1}$; UV (MeOH) $\lambda_{max}$ (log ε): 206.3 (0.69), 210.2 (0.64), 254.3 (0.13), 270 (0.05) nm; EIMS m/z 472.5 [M]$^{\cdot+}$.

2) Sodium hydroxide (1N) with silver nitrate as catalyst were added to a mixture of halogenate product of compounds with formula I (0.1 mol) in montmorillonite. The reaction mixture was heated to 96° C. for 3-5 h. The product was then extracted with DCM and MeOH. The combined organic phases were concentrated in vacuo to give rough products. The products were then subjected to silica gel chromatography to give pure compounds with formula IV.

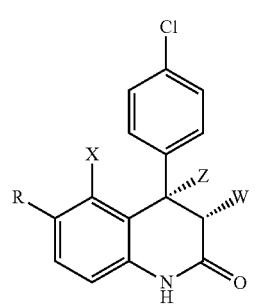
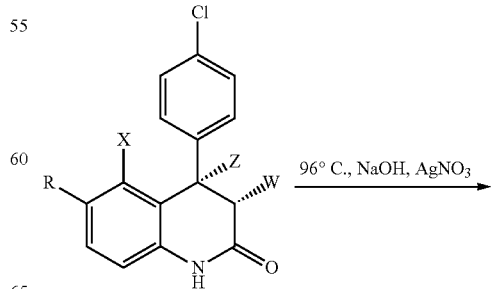

-continued

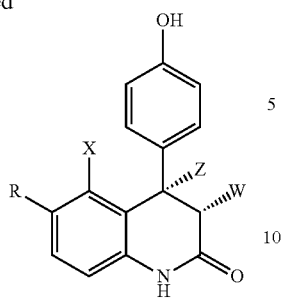

The compounds were characterized by the following spectroscopic data:

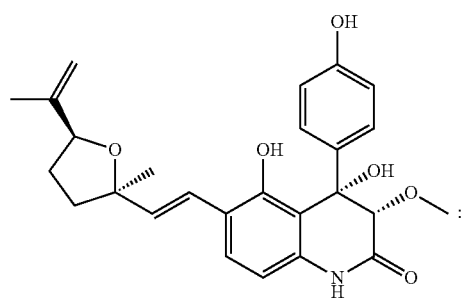

$[\alpha]^{24}_D = +140$ (c 0.016, MeOH); IR(KBr) $v_{max}$ 3340, 2929, 1650, 1410 and 1105 cm$^{-1}$; UV (MeOH) $\lambda_{max}$ (log ε): 206.8 (0.69), 215.2 (0.64), 250 (0.13), 272 (0.05) nm; EIMS m/z 452 [M]$^{\cdot+}$.

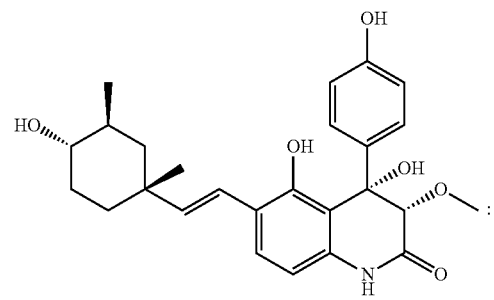 [SMILES: CO[C@@H]1C(=O)Nc2ccc(/C=C/[C@]3(C)CC[C@H](O)[C@@H](C)C3)c(O)c2[C@@]1(O)c1ccc(Cl)cc1]

$[\alpha]^{24}_D = +142$ (c 0.012, MeOH); IR(KBr) $v_{max}$ 3345, 2900, 1650, 1400 and 1125 cm$^{-1}$; UV (MeOH) $\lambda_{max}$ (log ε): 210.4 (0.69), 211.5 (0.64), 254 (0.13), 270 (0.05) nm; EIMS m/z 453.6 [M]$^{\cdot+}$.

Compounds with Formula V

Compounds with formula I, II, III or IV (0.1 mol) were dissolved in MeOH, and Pd/C (10%) was added. The reaction mixture was stirred at room temperature under H$_2$ overnight, then filtered. The filtrate was concentrated in vacuo and then subjected to silica gel chromatography to give pure compounds with formula V.

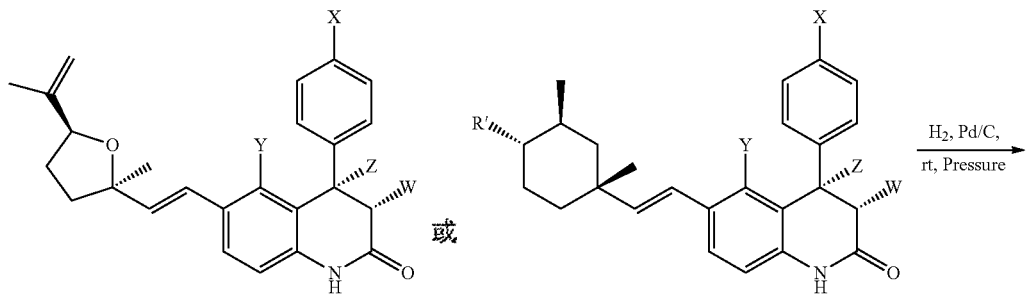

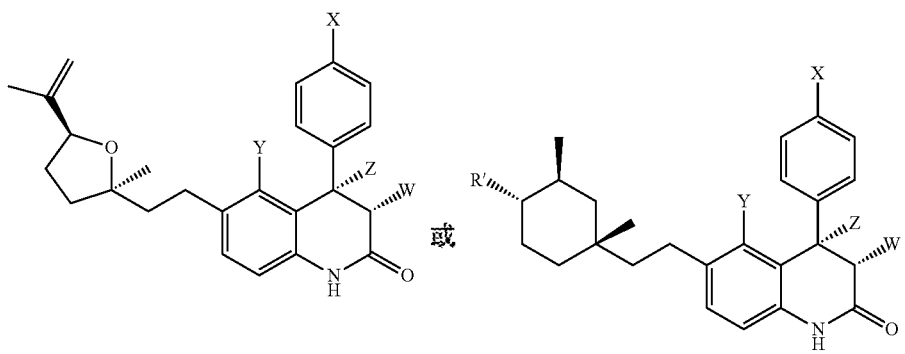

The compounds were characterized by the following spectroscopic data:

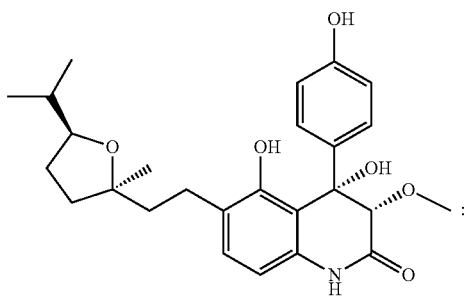

colorless crystal; $[\alpha]^{24}_D$=+133.5 (c 0.017, MeOH); IR (KBr) $v_{max}$ 3288, 2970, 1721, 1618, 1379 and 1082 cm$^{-1}$; UV (MeOH) $\lambda_{max}$ (log ε): 211 (0.41), 233.6 (0.26), 280.9 (0.20), 285 (0.19), 322 (0.21) nm; EIMS m/z 440.2 [M]$^{\cdot+}$.

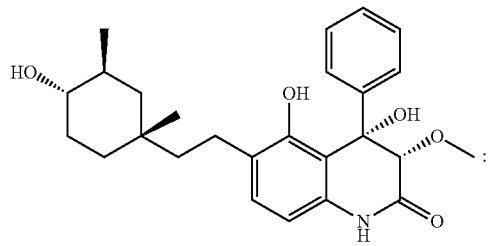

white powder; $[\alpha]^{24}_D$=+133.5 (c 0.017, MeOH); IR(KBr) $v_{max}$ 3366, 2926, 1600, 1421 and 1105 cm$^{-1}$; UV (MeOH) $\lambda_{max}$ (log ε): 204.8 (0.69), 211.2 (0.64), 253 (0.13), 280 (0.05) nm; EIMS m/z 440 [M]$^{\cdot+}$.

Unspecified chemical reaction conditions and separation strategies for the compounds provided herein are routine operation in pharmaceutical chemistry that would be readily apparent to those of ordinary skill in this field. Accordingly, one of ordinary skill in the art would readily adjust or modify the above preparation methods according to actual situation.

Example 4

In Vivo Antiviral Activity Against HSV-1

The antiviral activities against HSV-1 were evaluated by a cytopathic effects (CPE) assay. Hep-2 monolayer cells were cultured with trypsin enzyme-digesting technique and transferred to 96-well plates. The HSV-1 virus was seeded in Hep-2 cells in 96-well plates, with 2% RPMI-1640 medium, and incubated at 37° C., 5% $CO_2$. After more than 90% lesions, the virus-infected cells were repeatedly frozen and thawed 3 times, centrifuged, quantitative packed and stored at −80° C. Each tested compound was dissolved in 10 μl DMSO to make a homogeneous solution and the solution was diluted 10 times by half-and-half dilution with 2% RPMI-1640 medium. The gradient solution was added to the infected cells incubated in 96-well plates, Ribavirin was used as positive control. Normal cells were used as blank control. Infected cells were used as negative control. All samples were incubated at 37° C., 5% $CO_2$. Pathological changes were observed once every hour, for 24 h. After 90% lesions in negative control, 1% neutral red was added after removal of liquid in 96-well plates. The OD value was determined at 540 nm. $IC_{50}$ values of tested compounds were calculated by Reed-Muench methods.

The results indicated that the quinolinone derivatives showed different inhibitory activities against HSV-1 virus with $IC_{50}$ values on a scale of 0.07-100 μM. Especially, compounds with formula I exhibited more potent anti-HSV-1 activity than ribavirin ($IC_{50}$=78 μM), with $IC_{50}$ values of 0.07 and 0.21 μM. The results show that alkaloids provided herein have potent anti-HSV-1 activities, and would be useful as anti-viral agents, for example, anti-HSV-1.

TABLE 1

Anti-HSV-1 Activities of Compounds With Formula I

| | $IC_{50}$ (μM) | $TC_{50}$ (μM) | SI |
|---|---|---|---|
| (structure 1) | 0.07 | 64.94 | 955 |
| (structure 2) | 0.21 | 36.9 | 179 |
| Ribavirin | 78 | >10$^4$ | >128 |

What is claimed is:
1. A method of treating an infection of Herpes Simplex Virus 1 (HSV-1), comprising administering to a subject in need thereof an effective amount of a compound, or pharmaceutically acceptable salts thereof, wherein the compound, or pharmaceutically acceptable salts thereof, has a structure of the following formula,
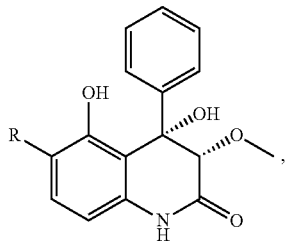
Formula I
wherein R is
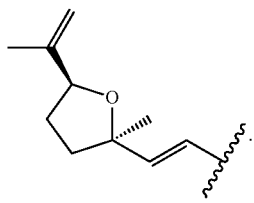 [SMILES: */C=C/[C@@]1(C)CC[C@@H](C(=C)C)O1]
* * * * *